(12) United States Patent
O'Connor

(10) Patent No.: US 6,491,712 B1
(45) Date of Patent: *Dec. 10, 2002

(54) DOUBLE WALLED BALLOON DEBRIS COLLECTOR

(76) Inventor: Lawrence R. O'Connor, 1636 Virginia Ave., Glendale, CA (US) 91202

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/625,383

(22) Filed: Jul. 26, 2000

(51) Int. Cl.[7] ............................................. A61M 29/00
(52) U.S. Cl. ..................................................... 606/200
(58) Field of Search ........................ 606/200, 1, 191, 606/192, 194, 198, 127, 114, 113

(56) References Cited

U.S. PATENT DOCUMENTS 4,469,100 A * 9/1984 Hardwick .................. 606/194
5,947,995 A * 9/1999 Samuels .................... 606/200

* cited by examiner

Primary Examiner—Kevin T. Truong
(74) Attorney, Agent, or Firm—John E. Wagner; Robert C. Smith

(57) ABSTRACT

A device for collecting debris flowing in an artery downstream from a percutaneous coronary intervention includes a hollow guidewire, a double walled balloon connected to the guidewire, and a filter secured to the balloon and to the guidewire, all of which are inserted into the artery downstream of the intervention. Prior to the intervention, the double walled balloon is inflated to occlude the blood vessel except for the open area of the filter. Any debris flowing downstream from the intervention is caught in the filter. When the intervention is completed, the balloon is deflated causing it to collapse away from the vessel wall, permitting blood flow past itself and trapping any debris caught by the filter between itself and the guidewire. Multiple inflation and deflation cycles may be performed if multiple interventions are required upstream. The entire device can then be removed from the artery.

14 Claims, 2 Drawing Sheets

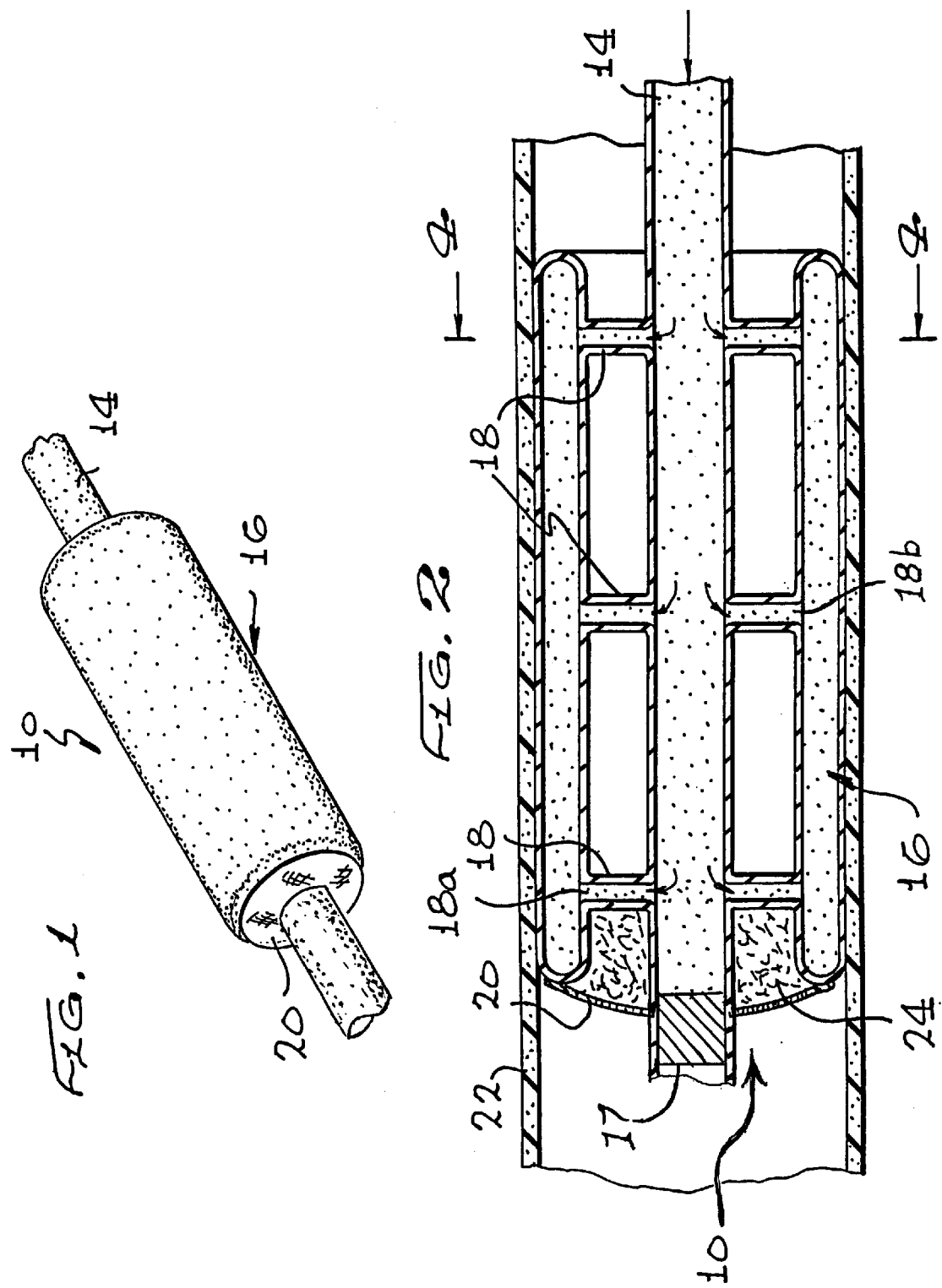

DOUBLE WALLED BALLOON DEBRIS COLLECTOR

BACKGROUND OF THE INVENTION

The practice of performing balloon angioplasty as a means of opening blood vessels, which are partially or substantially blocked by plaque, is well known. The biggest problem or risk factor in connection with such percutaneous intervention is downstream embolization of material that collects in and on unstable plaque. Either spontaneously or during a coronary intervention where the plaque is being treated, this material, which consists of blood clot and cholesterol emboli fragments is often being shed downstream. The end result of this appears to be micro-infarction of the territory served by the artery being treated. This, in turn, leads to a heterogeneity of electrical conduction and the creation of a myocardial substrate that makes the patient prone to ventricular arrhythmias, namely ventricular tachycardia or fibrillation. This may explain the small incidence of cardiac death that occurs late after coronary intervention.

As a result of the foregoing, it has been proposed to utilize some form of filter or catcher to collect the particles and debris that tend to break loose. Various approaches have been proposed, such as hanging a basket, a filter or an umbrella on the guidewire, but none seem to work. The reason is that they don't totally occlude the blood vessel and thus some of the debris gets by. It has been proposed to insert a balloon on a guidewire, which occludes the vessel and then an export catheter is brought down the guidewire, after the intervention and the blood that has collected upstream of the balloon is suctioned out. The problem with this approach is that, while the balloon is inflated, there is no blood flow downstream. The time during which the vessel is occluded is at least about four minutes and this may pose a real risk to the patient. Much longer intervals are likely, if for any reason, the intervention does not go well.

Thus, there is a need for a device and process which can provide a reasonable assurance of catching and removing such debris from blood vessels without significant added risk to the patient.

BRIEF SUMMARY OF THE INVENTION

It occurred to the applicant that what was needed was a double walled balloon having a filter on its downstream end placed downstream of any such intervention. The balloon would conform to the inside dimensions of the artery to block any bypass flow, thereby forcing all of the blood flowing downstream from the intervention through the hollow interior of the double walled balloon to the filter. The debris would be captured on the upstream side of the filter, while permitting an adequate amount of blood to flow downstream through the filter.

Since the double walled balloon must be inflated and deflated, applicant has designed the double walled balloon to be supported on the shaft of a 0.014 nitinol tube. The nitinol tube performs as would a normal solid core guidewire, but the central channel permits inflation and deflation of the balloon with radiographic contrast, and thus facilitates visual positioning under fluoroscopy. When the upstream intervention has been completed the balloon is deflated, thereby trapping the debris inside the two cisterns of the balloon filter. The balloon-filter can then be withdrawn from the artery and the debris examined.

Thus, although the double walled balloon and filter totally occlude the artery except for the filter, there is substantial surface area at the mesh or filter, and one can perform many possible intervention processes upstream, since the filter can catch and trap any debris resulting from such processes. Additionally, if multiple sequential interventions are performed upstream, the balloon filter may be deflated and reinflated and the debris remains trapped in the cisterns. The deflation cycle facilitates blood flow downstream.

BRIEF DESCRIPTION OF THE DRAWINGS

FIG. 1 is a perspective view of my double walled balloon structure mounted on a guidewire;

FIG. 2 is a cross-sectional view of the device of FIG. 1;

DETAILED DESCRIPTION OF THE PREFERRED EMBODIMENT

Figure 4:
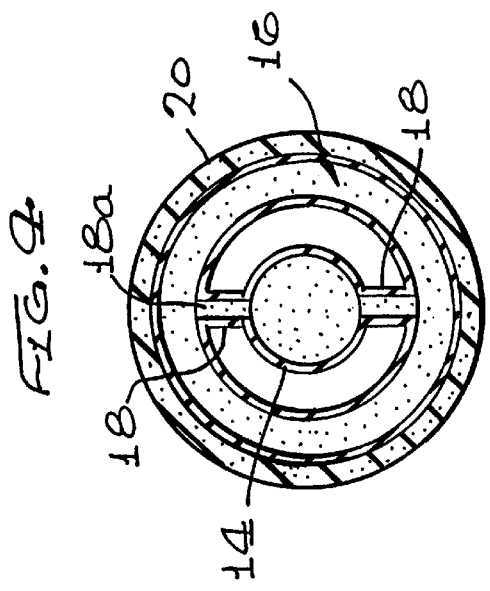
FIG. 4 is a right-end view of the device of FIGS. 1, 2 and 3.

FIG. 1 is a perspective view of my debris-catching device 10 shown mounted on a guidewire 14, which may be a 0.014" nitinol tube; and FIG. 2 is a longitudinal sectional view therethrough. Since the guidewire 14 is hollow, radiographic contrast material (hereafter, contrast) can be supplied through it to inflate a double walled balloon 16, which is closed by any convenient means, such as a plug 17. Guidewire 14 has a number of ports, 18a and 18b, which communicate water or contrast through a number of flexible passageways 18 to and from the interior of the double walled balloon 16 from guidewire 14. At the downstream end of the double walled balloon 16 is affixed a filter or mesh 20, which will permit blood to flow past itself, but which will block passage of any debris, such as that described above.

The filter is sized to block any particles larger than about 10 microns. The filter must also be firmly secured to guidewire 14. A modification of the balloon and filter would create the filter as an end wall of the double walled balloon, which is then perforated by means of a laser or other suitable means to form the mesh or filter 20.

Figure 3:
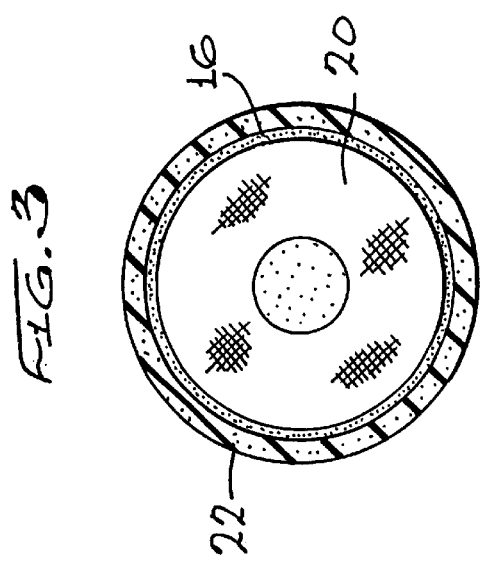
FIG. 3 is a left-end view of the device of FIGS. 1 and 2.

FIG. 3 is a view, partly in section, from the left or downstream end of the device 10, as installed in an artery 22. Visible in this view are the filter 20, the balloon 16, and the artery 22.

FIG. 4 is a sectional view taken along line 4—4 of FIG. 2. This view shows, in section, artery 22, the guidewire 14, double walled balloon 16 with openings 18a and passageways 18 communicating guidewire 14 with the interior of double walled balloon 16 and artery 22. It will be seen from FIGS. 2 and 4 that contrast will flow to and from guidewire 14 through passageways 18 to the chamber between the walls of the double walled balloon 16 to inflate or deflate the balloon.

Figure 5:
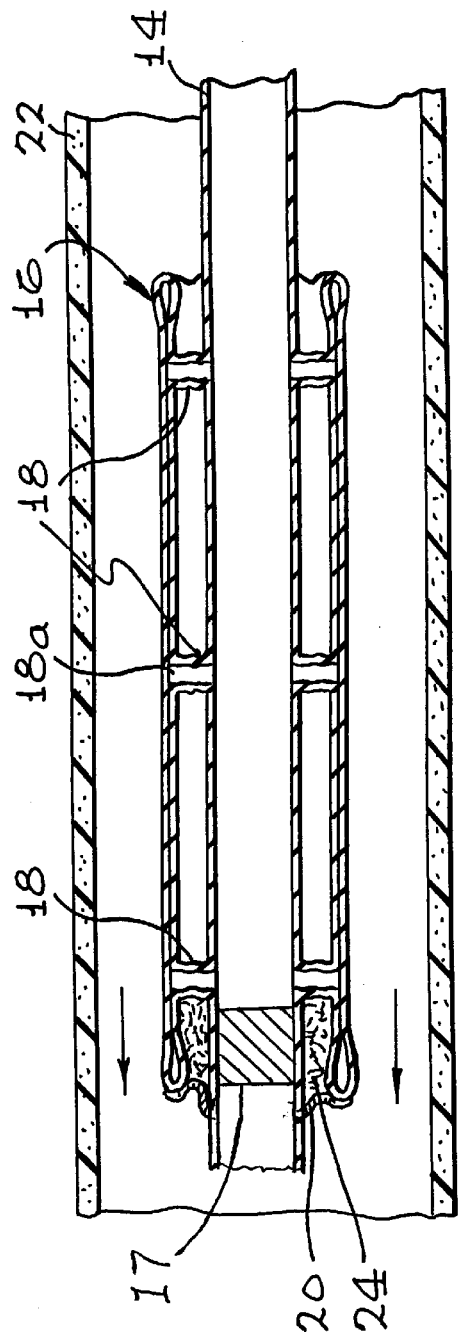
FIG. 5 is a cross-sectional view similar to FIG. 3 but with the balloon deflated.

FIG. 5 is a view similar to FIG. 2 showing all the same parts but with the double walled balloon 16 deflated. It will be observed that balloon 16, including mesh or filter is collapsed over and around the debris 24. Where there are no passageways 18, or if passageways 18 are very soft, the double walled balloon will collapse against guidewire 14. This also collapses the outer wall of balloon 16 away from the inside wall of artery 22 permitting substantial blood flow past balloon 16.

Debris 24 is effectively trapped between balloon 16 and guidewire 14, such that it cannot get into the bloodstream when the device 10 is deflated and/or removed from artery 22. It will be apparent that a very significant advantage of using applicant's device, as described, is that all the debris is captured and removed and it is available for examination, if desired.

While the mesh 20 is shown as a simple screen, it could be made of some significant length, such as 20 mm, in which case it would extend downstream from balloon 16 and would have considerable area for blood to flow through, despite filtering out a significant amount of debris. The mesh 20 could be of the same material as the balloon 16.

In operation, guidewire 14 is fed through the artery 22 to a position somewhat downstream of the location where the intervention is planned, guidewire 14 carrying the collapsed double walled balloon 16 and filter or mesh 20. When the balloon catheter reaches a desired location downstream of the intended intervention area, an additional catheter is inserted into the artery carrying whatever tool may be required to accomplish the purpose of the desired intervention. When the additional catheter is in place and it is desired to begin the intervention process, the device 10 is inflated, occluding the vessel except for the open area of the filter. If the process is to break up plaque upstream of the device 10, it is likely that some plaque or thrombus fragments may tend to move downstream where they would be caught by the filter 20.

One may desire to change the tools used upstream, in which case the double walled balloon 16 could be deflated for the period during which the tools are being changed, since the plaque is not being treated during that time. This would permit blood flow over the deflated balloon, as described above. The balloon would then be reinflated to catch any further debris. Alternatively, one could leave the balloon inflated since in most cases there should be adequate flow through the filter.

In some situations, the intervention could create enough debris to substantially or totally block the filter. In such case, the device could be deflated and removed and a new guidewire, balloon, and filter inserted in the artery.

The above-described embodiments of the present invention are merely descriptive of its principles and are not to be considered limiting. The scope of the present invention instead shall be determined from the scope of the following claims including their equivalents.

What is claimed is:

1. A device for collecting debris flowing downstream in an artery during coronary intervention comprising:
   a hollow guidewire positioned in said artery downstream of said intervention;
   a double walled balloon having an inside wall, an outside wall, an interior chamber between its walls and conduit means connecting said chamber to the interior of said guidewire to provide an inflation path between the interior of said guidewire and said interior chamber; and
   a filter secured to said guidewire and to said balloon on the downstream end of said balloon, such that when said balloon is inflated, said artery is occluded except for flow through said filter.

2. A device as claimed in claim 1 wherein said guidewire constitutes a supply conduit connected to said conduit means for inflating said balloon.

3. A device as claimed in claim 2 wherein deflating of said balloon causes said balloon to collapse around and over said guidewire and capture any debris collected by said filter.

4. A double walled balloon catheter as claimed in claim 1 wherein said filter is secured to the downstream end of said balloon and to said guidewire.

5. A device for collecting debris flowing downstream in a coronary artery during coronary intervention comprising:
   a hollow guidewire having a single internal passageway constituting a supply conduit positioned in said artery;
   a balloon secured to said guidewire having an elongated outer wall for engagement with the inner surface of said artery and an inner wall defining a passage through said balloon and having an internal chamber between its walls operatively connected to said supply conduit; and
   a filter secured to said guidewire and to the downstream end of said balloon, such that when said balloon is inflated, all flow through said artery must flow through said filter, and when said balloon is deflated, said balloon is collapsed against said guidewire, thereby trapping said debris while permitting flow past said balloon.

6. A device as claimed in claim 5 wherein said supply conduit is connected to a source of radiographic contrast material.

7. A device for collecting debris flowing downstream in a coronary artery during percutaneous coronary intervention comprising:
   a hollow guidewire having a single internal passageway constituting a supply conduit positioned in said artery;
   a double walled balloon having an inner wall and an outer wall secured to said guidewire and having a chamber between its walls operatively connected to said supply conduit; and
   a filter secured to the downstream end of said double walled balloon, such that when said balloon is inflated, its outer wall contacts the inside wall of said artery, thereby blocking all flow through said artery except that flowing through said filter and debris flowing in said artery is captured on the upstream side of said filter.

8. A device as claimed in claim 7 wherein deflating of said balloon causes said balloon to collapse around and over said guidewire and trap any debris collected by said filter.

9. A double walled balloon catheter including a balloon body having an elongated inner wall and an elongated outer wall, said walls being joined at their ends to define an inflation chamber, said balloon catheter, when inflated, defining a flow passage through an artery;
   an inflation port in said body communicating with said inflation chamber;
   a hollow guidewire having a single internal passageway comprising a supply conduit positioned internally of said elongated inner wall and a conduit connecting said inflation port to said passageway to thereby define an inflation path between the interior of said guidewire and said inflation chamber; and
   a filter bridging said flow passage to filter debris flow through said flow passage when said balloon body is inflated and when said balloon body is deflated said walls are collapsed to trap said debris.

10. A double walled balloon catheter as claimed in claim 9 wherein when said balloon body is inflated, said outer wall engages said artery and flow through said artery must flow through said filter.

11. A double walled balloon catheter as claimed in claim 10 wherein when said balloon is deflated said outer wall collapses away from said artery and permits flow between said outer wall and said artery.

12. A double walled balloon catheter as claimed in claim 9 further comprising a passageway connecting said port with said hollow guidewire.

13. A double walled balloon catheter, including an elongated balloon body having an outer tubular wall for engaging the inner wall of an artery when the balloon catheter is inflated and an inner tubular wall;

said outer and inner tubular walls being joined at their end regions to define and to close an elongated balloon inflation chamber;

said inner wall defining a flow passage through said artery when said balloon body is inflated;

a plurality of inflation ports in said body communicating with said elongated balloon inflation chamber;

a hollow guidewire internal of said inner tubular wall, a plurality of ports in the wall of said guidewire and passageways connected to said ports and to said inflation ports to provide inflation paths between the interior of said guidewire and said elongated balloon inflation chamber;

a filter secured to the downstream end of said balloon and to said guidewire bridging said flow passage whereby said filter is positioned to filter flow through said flow passage when said balloon body is inflated and said filter and balloon body capture filtered material when said balloon body is deflated for removal with said balloon catheter.

14. A double walled balloon catheter including a balloon body having an elongated inner wall and an elongated outer wall, said walls being joined at their ends to define an elongated inflation chamber, said balloon body, when inflated, defining a flow passage through said artery;

inflation means for inflating and deflating said balloon comprising a port in said balloon body and a hollow guidewire including an opening operatively connected to said port; and a filter bridging said flow passage to filter debris flowing through said flow passage when said balloon is inflated and when said balloon body is deflated, said walls are collapsed to trap said debris;

wherein said filter is secured to the downstream end of said balloon and to said guidewire; and wherein said filter is secured to the downstream end of said balloon and to said guidewire.

* * * * *